US009744582B2

(12) United States Patent
LeFevere et al.

(10) Patent No.: US 9,744,582 B2
(45) Date of Patent: Aug. 29, 2017

(54) WEAR TOLERANCE INDICATOR FOR STAMPING DIES

(71) Applicants: Michael W LeFevere, Imlay City, MI (US); Raymond Slowik, Royal Oak, MI (US)

(72) Inventors: Michael W LeFevere, Imlay City, MI (US); Raymond Slowik, Royal Oak, MI (US)

(73) Assignee: FCA US LLC, Auburn Hills, MI (US)

( * ) Notice: Subject to any disclaimer, the term of this patent is extended or adjusted under 35 U.S.C. 154(b) by 281 days.

(21) Appl. No.: 14/265,718

(22) Filed: Apr. 30, 2014

(65) Prior Publication Data

US 2015/0314359 A1 Nov. 5, 2015

(51) Int. Cl.

*B21D 37/12* (2006.01)
*G01N 3/56* (2006.01)
*B30B 15/06* (2006.01)
*B30B 15/02* (2006.01)

(52) U.S. Cl.

CPC .............. *B21D 37/12* (2013.01); *B30B 15/02* (2013.01); *B30B 15/065* (2013.01); *G01N 3/56* (2013.01)

(58) Field of Classification Search

CPC ........ B21D 37/12; B21D 37/00; B21D 37/02; B21D 37/10; G01N 3/56; B26D 5/08; B21J 13/04; B30B 1/00; B23Q 17/00; B23Q 23/00

USPC ...... 72/361, 31.01, 462, 470, 476, 446, 455, 72/456

See application file for complete search history.

(56) References Cited

U.S. PATENT DOCUMENTS 2,233,403 A * 3/1941 Dickinson ................ G01N 3/56 138/36
2,925,305 A * 2/1960 Hackman ................ B22C 23/00 384/41
3,070,404 A * 12/1962 Moyer .................. B21D 37/10 384/30
3,118,217 A * 1/1964 Gardner ................ B21D 37/10 29/432
4,103,539 A * 8/1978 Worley .................. B04C 11/00 116/208
4,174,199 A 11/1979 Benninghaus
4,530,655 A 7/1985 Hehl
4,573,901 A 3/1986 Hehl
4,756,630 A * 7/1988 Teeslink ................ B21D 28/12 384/29

(Continued)

*Primary Examiner* — Dmitry Suhol
*Assistant Examiner* — Peter Iannuzzi
(74) *Attorney, Agent, or Firm* — Ralph E Smith

(57) ABSTRACT

A stamping die includes an upper die member, a lower die member, and at least one guidance member operably disposed to guide relative movement between the upper and lower die members. The members are movable relative to one another in reciprocating motion along an axis to generate work-pieces. The guidance member has a guiding surface for guiding relative movement between the die members. The guidance member also has at least one wear indicator cavity recessed from the guiding surface. A depth of the wear indicator cavity corresponds to the extent of acceptable wear of the guiding surface. The cavity allows for visual inspection of the extent of wear of the at least one guidance member and thus obviates the requirement that the guidance member be removed from the stamping die for inspection.

18 Claims, 8 Drawing Sheets

(56) References Cited

U.S. PATENT DOCUMENTS

| | | | | |
|---|---|---|---|---|
| 4,941,344 | A * | 7/1990 | Beech | B21D 37/10 384/30 |
| 4,964,326 | A | 10/1990 | Steinhoff | |
| 5,267,384 | A * | 12/1993 | Teeslink | B21D 28/12 269/287 |
| 5,451,110 | A * | 9/1995 | Gams, Jr. | B02C 2/06 116/208 |
| 7,351,055 | B2 | 4/2008 | Yoshioka | |
| 2004/0091215 | A1 * | 5/2004 | Barnoski | B21D 28/02 385/78 |
| 2005/0056420 | A1 * | 3/2005 | Ramey | E21B 3/04 166/250.05 |
| 2007/0199364 | A1 | 8/2007 | Norin | |

* cited by examiner 210
212
214
218
220
224
258
262

WEAR TOLERANCE INDICATOR FOR STAMPING DIES

FIELD

The present disclosure relates generally to structures that guide the motion of stamping dies, such as guidance plates or pins for the stamping dies.

BACKGROUND

A stamping die often includes two structures that are reciprocated back and forth with respect to one another. These structures are referred to as die shoes and each die shoe supports a die that dictates the shape of the metal blank to be stamped. The motion of the upper die shoe must be guided precisely. If the alignment of the upper and lower die shoes is not maintained, the metal between the die shoes will not flow within the stamping die as desired. For example, the metal work-piece will exhibit splits or tears if the motion of the upper die shoe is not controlled. The upper die shoe is guided in motion by structures such as plates or bushings. Over time, the surfaces of these guidance structures wear down and the extent of play or variation in the movement of the upper die shoe will increase. When parts out of tolerance are generated from the stamping die, several factors must be assessed to determine the source of the problem. The extent of wear of the guidance structures is one of the factors assessed. However, the assessment of the surfaces of these guidance structures is time-consuming. The guidance structures must be removed from the stamping die and the dimensions across the full length of the guiding surfaces must be completed, such with a micrometer or caliper.

SUMMARY

In one aspect, a stamping die is provided in accordance with the teachings of the present disclosure. In an exemplary implementation, the stamping die includes an upper die member, a lower die member, and at least one guidance member operably disposed to guide relative movement between the upper and lower die members. The upper and lower die members are movable relative to one another in reciprocating motion along an axis to generate work-pieces. The guidance member has a guiding surface for guiding relative movement between the upper and lower die members. The guidance member also has at least one wear indicator cavity recessed from the guiding surface. The depth of the at least one wear indicator cavity corresponds to the extent of acceptable wear of the guiding surface. The guidance member is replaced or refurbished when the cavity is no longer discernible. The cavity allows for visual inspection of the extent of wear of the at least one guidance member while the at least one guidance member is operably disposed on the stamping die. The cavity thus obviates the requirement that the guidance member be removed from the stamping die and inspected to determine if the guidance member is within acceptable wear tolerance.

In some implementations, the wear indicator cavity can be formed as a channel or a circle. Further, in some implementations, a plurality of wear indicator cavities can be formed in a single guidance member. Such an implementation can be desirable since uneven wearing across the plurality of wear indicator cavities can reveal potential misalignment condition affecting the performance of the stamping die.

In another aspect, a method is provided in accordance with the teachings of the present disclosure. In an exemplary implementation, the method includes the step of moving an upper die member and a lower die member relative to one another in reciprocating motion along an axis to generate work-pieces. The method also includes the step of guiding relative movement of the upper and lower die members with at least one guidance member having a guiding surface. The method also includes the step of disposing at least one visually-detectable wear indicator cavity in the guidance member recessed from the guiding surface. A depth of the at least one wear indicator cavity from the guiding surface corresponds to an extent of acceptable wear of the guiding surface. The method also includes determining whether the guiding surface is within the extent of acceptable wear by detecting whether the wear indicator cavity remains recessed below the guiding surface.

In some implementations, the visually-detectable wear indicator cavity can be provided as being open to the guiding surface. The cavity can be formed, for example, as a channel or a cylinder. In other implementations, the visually-detectable wear indicator cavity can be provided with a plurality of differently colored layers. A junction of two layers is defined at the depth of acceptable wear tolerance.

Further areas of applicability of the teachings of the present disclosure will become apparent from the detailed description, claims and the drawings provided hereinafter, wherein like reference numerals refer to like features throughout the several views of the drawings. It should be understood that the detailed description, including disclosed embodiments and drawings referenced therein, is merely exemplary in nature intended for purposes of illustration only and are not intended to limit the scope of the present disclosure, its application or uses. Thus, variations that do not depart from the gist of the present disclosure are intended to be within the scope of the present disclosure.

DESCRIPTION

Figure 1:
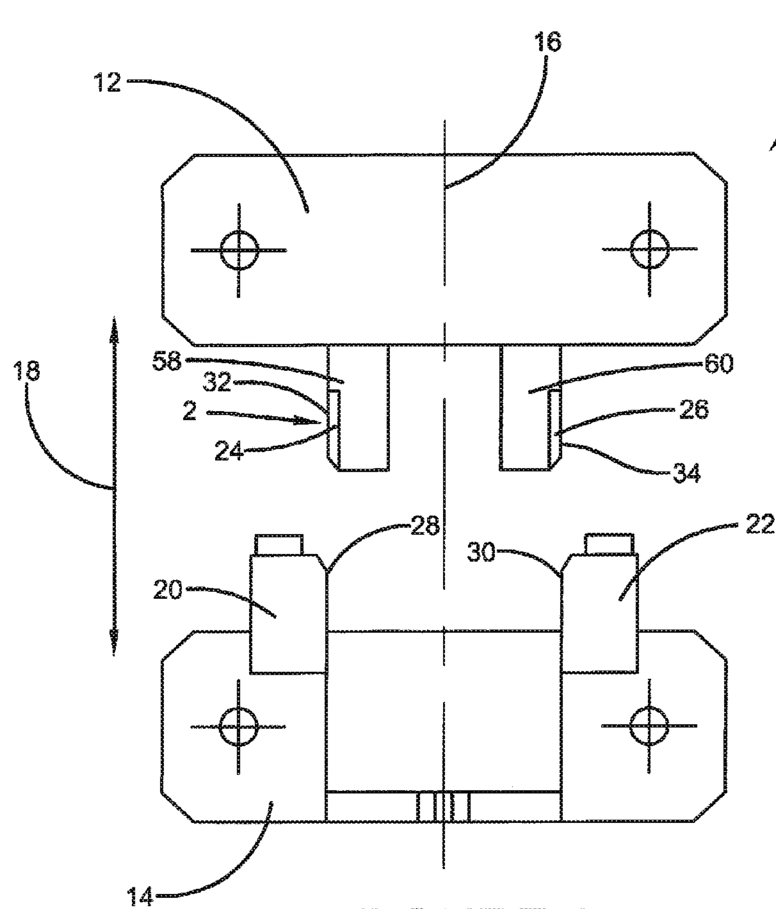
FIG. 1 is a front view of an exemplary stamping die with guidance members according to the principles of the present disclosure.

With initial reference to FIG. 1, an exemplary stamping die 10 is shown and includes an upper die member 12, a lower die member 14, and at least one guidance member operably disposed to guide relative movement between the upper and lower die members 12, 14. In one exemplary implementation, the upper and lower die members 12, 14 are upper and lower shoes. The upper and lower die members 12, 14 are reciprocated back and forth with respect to one another along an axis 16. The reciprocating movement is referenced at 18. A metal blank (not shown) is placed between the upper and lower die members 12, 14 and a work-piece is generated from the metal blank when the upper and lower die members 12, 14 are brought together. The work-piece is extracted from the stamping die 10 when the upper and lower die members 12, 14 are separated.

With continuing reference to FIG. 1, the stamping die 10 includes a plurality of guidance members 20, 22, 24, 26. Each of the guidance members 20, 22, 24, 26 has respective guiding surfaces 28, 30, 32, 34 operably disposed to guide relative movement between the upper and lower die members 12, 14. The guidance member 24 is inset into a plate holder portion 58 of the upper die member 12. The guidance member 26 is inset into a plate holder portion 60 of the upper die member 12. The guiding surface 28 is fixed with respect to the lower die member 14. The guiding surface 32 slides along the guiding surface 28 during at least part of the reciprocating movement.

The interaction of the guiding surfaces 28 and 32 assists in controlling the motion of the upper die member 12 along a desired path. Similarly, the guiding surface 30 is fixed with respect to the lower die member 14 and the guiding surface 34 is fixed with respect to the upper die member 12. The guiding surface 34 slides along the guiding surface 30 during at least part of the reciprocating movement. The interaction of the guiding surfaces 30 and 34 assists in controlling the motion of the upper die member 12 along a desired path. It will be appreciated that the stamping die 10 and other stamping dies or equipment discussed herein are examples of stamping equipment on which guidance members discussed herein are associated with and/or utilized.

Figure 2:
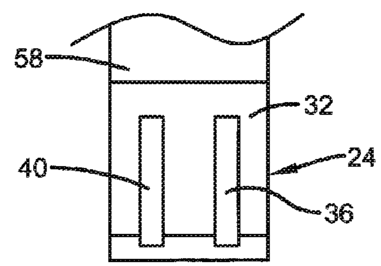
FIG. 2 is a partial side view of the stamping die and guidance members shown in FIG. 1 according to the principles of the present disclosure.
Figure 3:
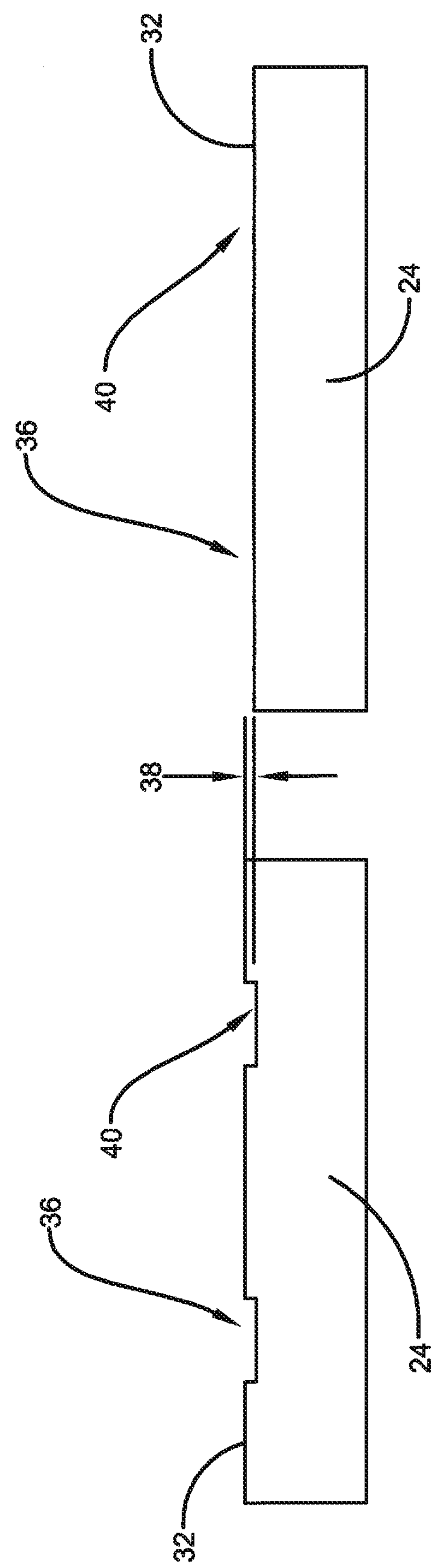
FIG. 3 is a side view of the guidance members according to the principles of the present disclosure.

With initial reference to FIGS. 2-3, the guidance member 24 includes at least one wear indicator recess or cavity 36. The wear indicator cavity 36 is recessed from the guiding surface 32. The wear indicator cavity 36 extends along the direction of reciprocating motion 18 of travel. Generally, the thickness of the guidance member 24 will diminish over time due to wear. It is noted that the size of the guiding surface of a guidance member is determined in view of the size of wear indicator cavity or cavities. In other words, if the loading on the guidance surface dictates a particular area for the guidance surface, the area of any wear indicator cavity detracts from the load-bearing area.

FIG. 3 is a comparative illustration of the guidance member 24. The guidance member 24 is shown generally in an initial condition on the left side of FIG. 3 and in a worn condition on the right side of FIG. 3. The wear indicator cavity 36 is formed to have a depth corresponding to the extent of acceptable wear of the guiding surface 32. The depth is referenced at 38. Reference numeral 36 is applied in the right side of FIG. 3 to indicate where the wear indicator cavity 36 previously existed.

The guidance member 24 is replaced or refurbished when the wear indicator cavity 36 is no longer discernible, as shown on the right side of FIG. 3. The wear indicator cavity 36 thus obviates the requirement that that guidance member 24 be removed from the stamping die 10 and inspected, such as with a micrometer or caliper. An operator of the stamping die 10 can easily and readily detect that the guidance member 24 is worn beyond acceptable tolerance, such as by visual inspection.

In accordance with various aspects of the present disclosure, visual inspection of the guidance members discussed herein provides for cost savings with respect to operation of the associated stamping dies. For example, when guidance members have to be removed for inspection of the extent of wear, the stamping die experiences downtime. Inspection costs also include operator downtime, the time of inspection personnel, and the operating time of the inspection machine. Embodiments of the present disclosure reduce the frequency that guidance members must be removed by providing the wear indicator cavity, which provides a visually identifiable indication of wear that can be discerned without having to remove the guidance member from the stamping die. Embodiments of the present disclosure allow a stamping die operator to more precisely identify the time that replacement or refurbishment of the guidance member is required.

With reference again to FIG. 1, the guidance members 20, 22, 24, 26 are formed from different materials in accordance with an aspect of the present disclosure. In this exemplary implementation, the guidance members 20, 22 are castings that are flame hardened. Wear indicator cavities defined in the guidance members 20, 22 are machined into the guidance members 20, 22 before hardening. The extent of wear of the guidance members 20, 22 is assessed on a multi-axis milling machine. Conversely, the extent of wear of the guidance members 24, 26 is assessed with hand tools such a caliper or micrometer, after removal from the upper die member 12. In this exemplary implementation, the guidance members 24, 26 are bronze.

The exemplary guidance members 24, 26 wear faster than the guidance members 20, 22. However, it is noted that the arrangement of guidance members can be alternated in other embodiments of the present disclosure. It is also noted that embodiments of the disclosure may be practiced in which all of the guidance members 20, 22, 24, 26 are configured similarly with respect to wear indicator cavities. For example, in the exemplary embodiment illustrated, the wear indicator cavities of the guidance members 20, 22, 24, 26 are similarly-shaped, but not interfering. Thus, in the exemplary embodiment, wear indicator cavities can be formed in all of the guidance members, not to overlap or impact on another, to permit visual inspections. It is noted that the wear indicator cavities of two opposing guidance members are arranged such that the wear indicator cavities do not overlap when the opposing guidance members are in contact with one another.

With continuing reference to FIGS. 1-3, the wear indicator cavity 36 is shaped as a groove or channel that extends along the axis 16 of reciprocating motion 18. The guidance member 24 further includes a second wear indicator cavity 40 that is shaped as a channel that extends along the axis 16. The wear indicator cavities 36, 40 are spaced from one another and extend parallel to the axis 16. If the guidance member 24 wears unevenly, the wear indicator cavities 36, 40 will diminish differently. This condition reveals that one or more other issues may be affecting the performance of the stamping die 10. For example, the guidance members 20, 24 may be misaligned or the relative movement between the die members 12, 14 may not be along a desired axis.

Figure 4:
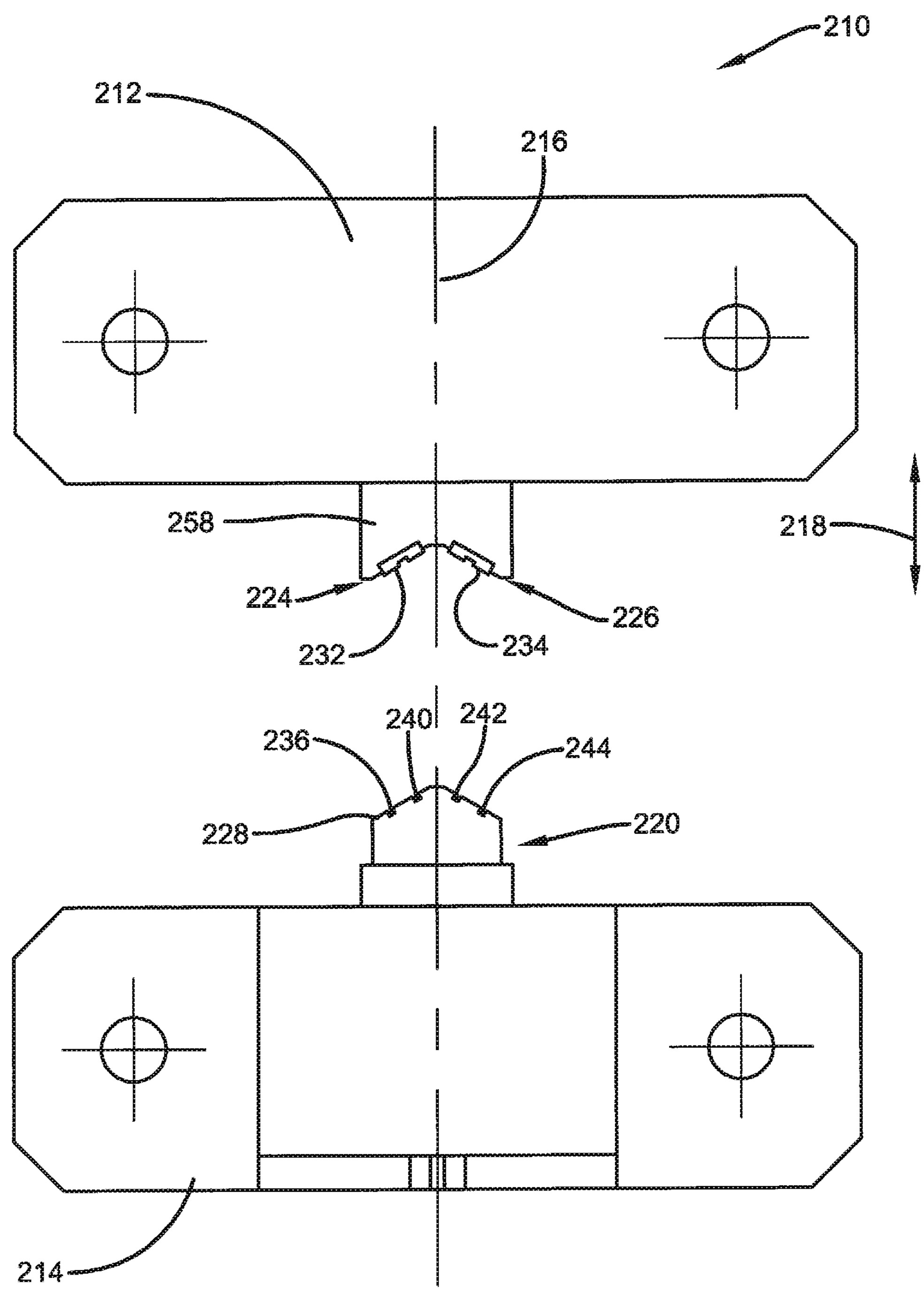
FIG. 4 is a front view of a second exemplary stamping die with guidance members according to the principles of the present disclosure.
Figure 5:
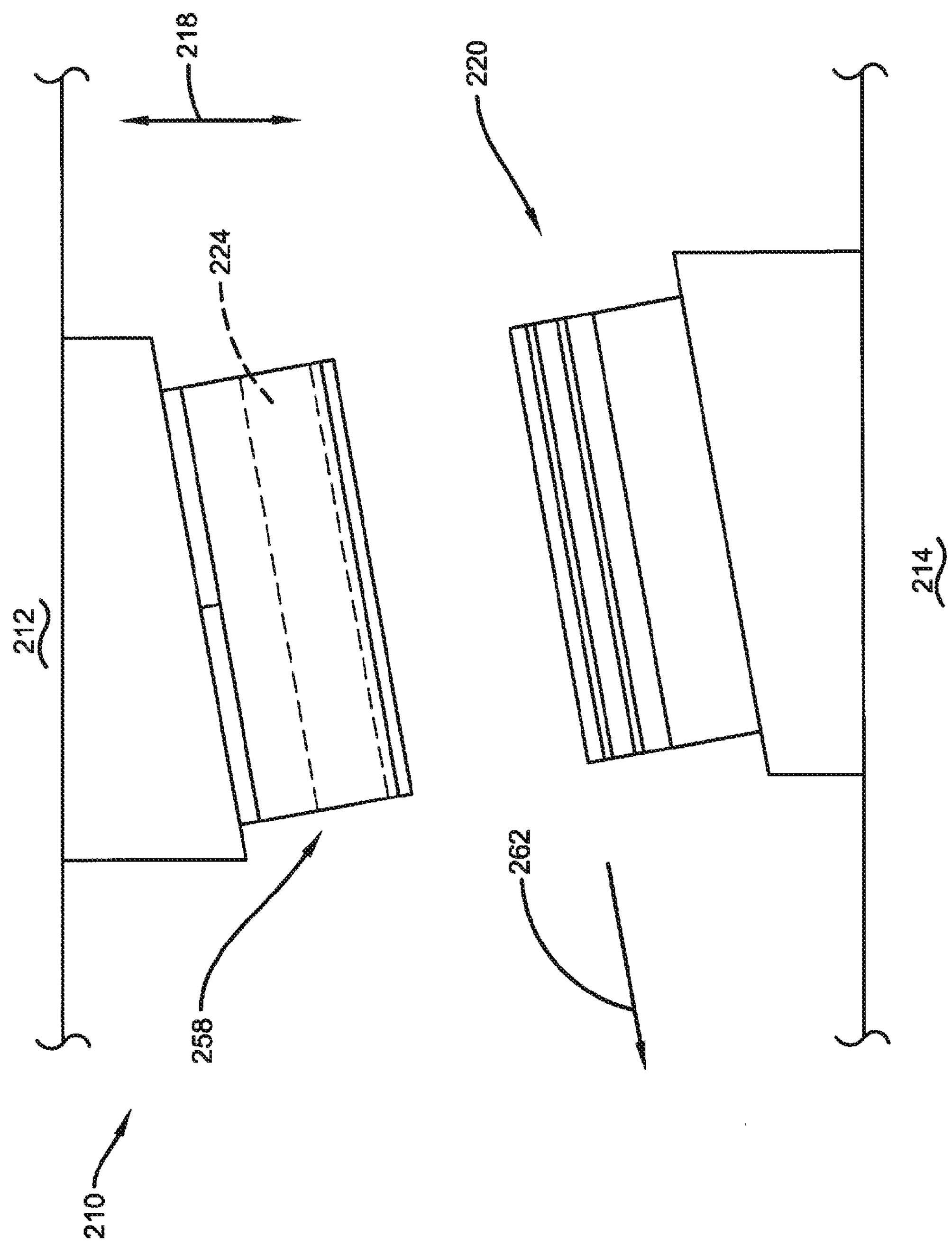
FIG. 5 is another view of the second exemplary stamping die shown in FIG. 4.
Figure 6:
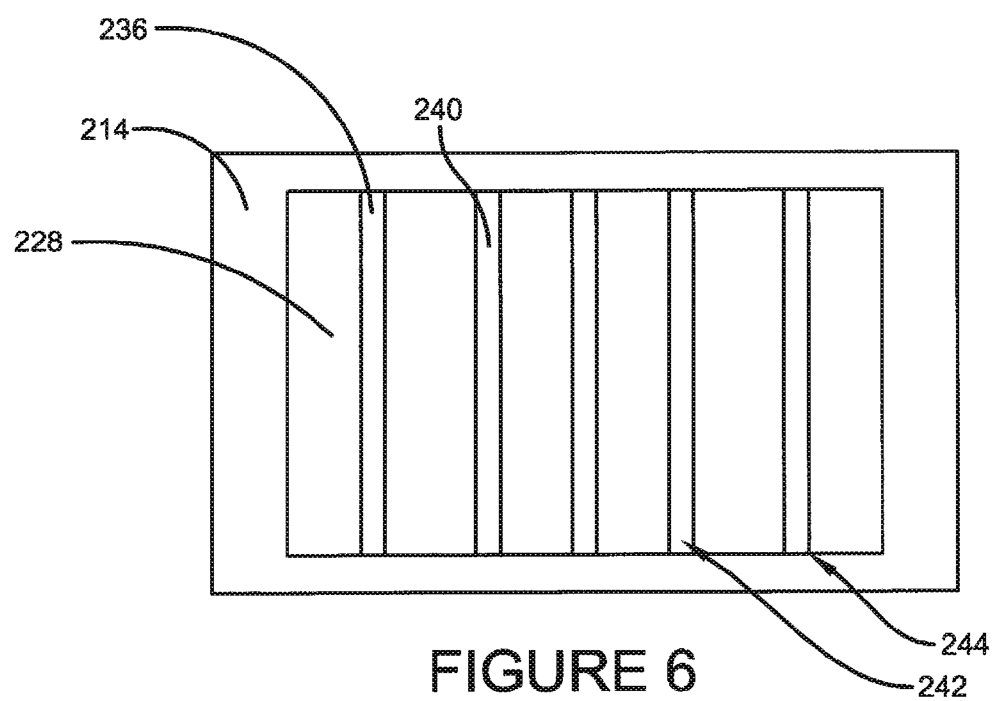
FIG. 6 is a top view of a portion of the second exemplary stamping die shown in FIG. 4.

With initial reference to FIGS. 4-6, an exemplary stamping die 210 includes an upper die member 212, a lower die member 214, and at least one guidance member operably disposed to guide relative movement between the upper and lower die members 212, 214. In one exemplary implementation, the upper and lower die members 212, 214 are upper and lower shoes. The upper and lower die members 212, 214 are reciprocated back and forth with respect to one another along an axis 216. The reciprocating movement is referenced at 218. A metal blank (not shown) is placed between the upper and lower die members 212, 214 and a work-piece is generated from the metal blank when the upper and lower die members 212, 214 are brought together. The work-piece is extracted from the stamping die 210 when the upper and lower die members 212, 214 are separated.

With continued reference to FIGS. 4-6, the stamping die 210 includes a plurality of guidance members 220, 224, 226. Each of the guidance members 220, 224, 226 has respective guiding surfaces 228, 232, 234 operably disposed to guide relative movement between the upper and lower die members 212, 214. The guidance members 224 and 226 are inset into a plate holder portion 258 of the upper die member 212.

With continued reference to FIGS. 4-6, the guidance member 220 includes wear indicator cavities 236, 240, 242, 244 formed in the guiding surface 228. FIGS. 4-6 confirm that embodiments of the disclosure can include wear indicator cavities in different planes. The wear indicator cavities 236, 240 extend in a first plane and the wear indicator cavities 242, 244 extend in a second plane, wherein the first and second planes are transverse to one another.

With continued reference to FIG. 5, the exemplary plate holder portion 258 is a moveable cam follower. The guidance member 220 is a cam, or driver. When the upper and lower die members 212, 214 come together, the plate holder portion 258 is urged in the direction referenced at 262. Thus, the wear indicator cavities 236, 240, 242, 244 extend along the direction of relative movement between the guiding surface 228 and the guiding surfaces 232, 234.

With continued reference to FIGS. 4-6, a benefit of visually monitoring wear in different planes is that if the guidance member 220 wears unevenly, the wear indicator cavities 236, 240, 242, 244 will diminish differently. As set forth above, uneven wear reveals that one or more other issues may be affecting the performance of the stamping die associated with the lower die member 214. By visually inspecting wear in different planes, the nature of the problem may be more easily detected. For example, wear patterns in the different planes may indicate the three-dimensional orientation of an undesired misalignment of guidance members or the direction of undesired relative movement between die members.

Figure 7:
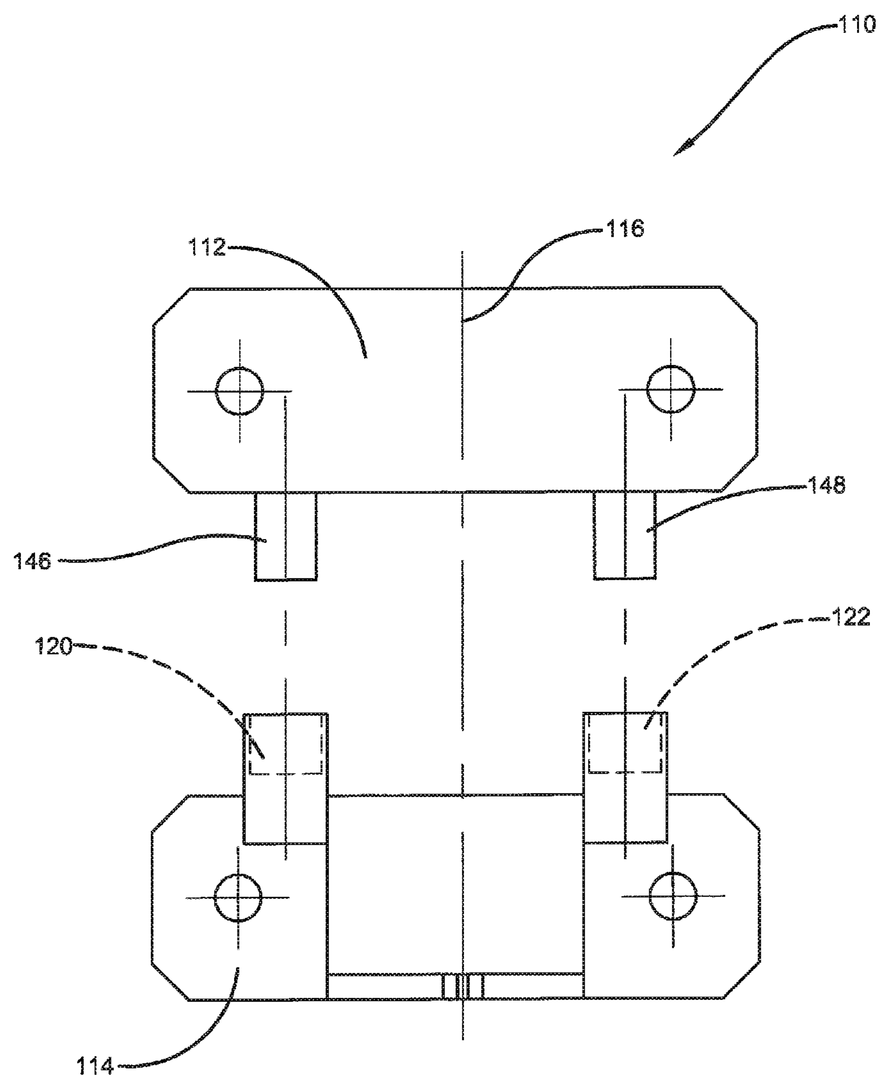
FIG. 7 is a front view of a third exemplary stamping die according to the principles of the present disclosure.
Figure 9:
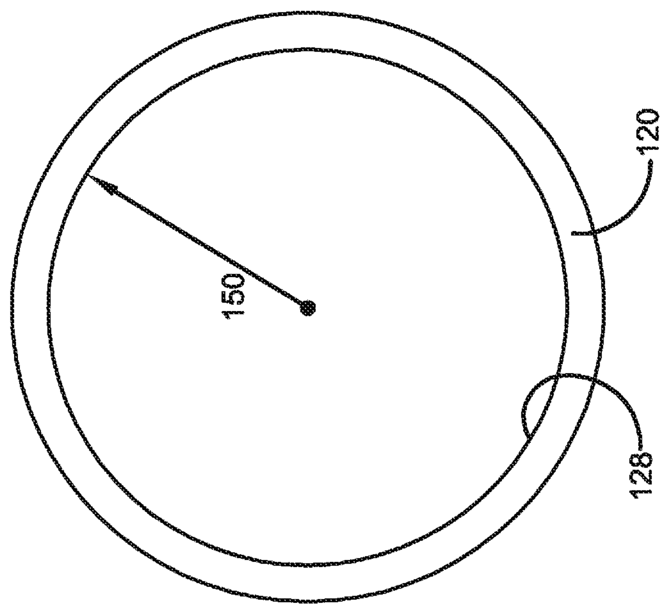
FIG. 9 is a second top view of the guidance member shown in FIG. 8 after use according to the principles of the present disclosure.
Figure 8:
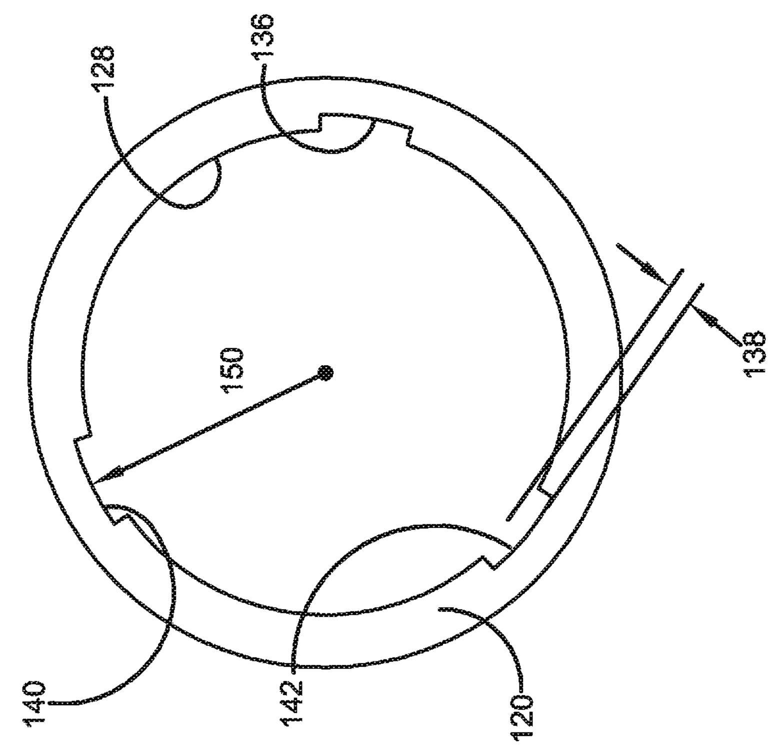
FIG. 8 is a top view of an exemplary guidance member according to the principles of the present disclosure.

With reference to FIGS. 7 and 8-9, an alternative embodiment of an exemplary stamping die 110 includes an upper die member 112, a lower die members 114, and guidance members 120, 122. In one exemplary implementation, the upper and lower die members 112, 114 are upper and lower shoes. The upper and lower die members 112, 114 reciprocate along an axis 116. The exemplary guidance members 120 and 122 are bushings and receive guide pins 146, 148 therein associated with the upper die member 112.

With initial reference to FIGS. 8 and 9, the guidance member 120 includes wear indicator cavities 136, 140, 142. The wear indicator cavities 136, 140, 142 are recessed from and evenly spaced about a guiding surface 128. In one exemplary implementation, the guiding surface 128 is an aperture. The wear indicator cavities 136, 140, 142 are shaped as channels. Generally, the thickness of the guidance member 120 will diminish over time due to wear. FIGS. 8 and 9 provide comparative illustrations of the guidance member 120. The guidance member 120 is shown generally in an initial condition in FIG. 8 and in a worn condition in FIG. 9. The wear indicator cavity 136 is formed to have a depth corresponding to the extent of acceptable wear of the guiding surface 128. The depth is referenced at 138. The radius of the bottom surface of the wear indicator cavity 136 is referenced at 150. The exemplary guidance member 120, having a plurality of wear indicator cavities 136, 140, 142, also provides the advantage noted above, wherein uneven wear among the wear indicator cavities 136, 140, 142 indicates, for example, potential misalignment in an associated stamping die.

Figure 10:
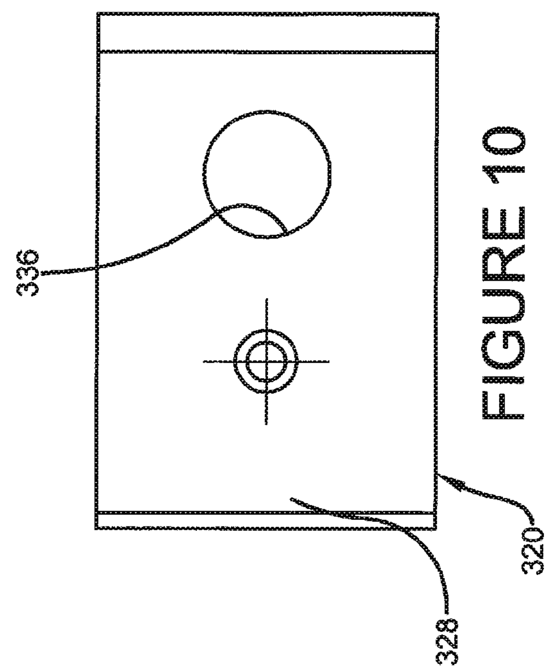
FIG. 10 is a top view of another exemplary guidance member according to the principles of the present disclosure.

With initial reference to FIG. 10, an alternative exemplary guidance member 320 is shown as an exemplary plate and includes a guiding surface 328. The guidance member 320 also includes a visually-detectable wear indicator cavity 336. In the exemplary implementation illustrated, the wear indicator cavity 336 is shaped as a cylinder or circle. If the guidance member 320 wears unevenly, the circumference of the wear indicator cavity 336 will diminish differently. This condition reveals that one or more other issues may be affecting the performance of the stamping die associated with the guidance member 320. It will be appreciated that while one visually-detectable wear indicator cavity 336 is shown associated with guidance member 320, guidance member 320 may include a plurality of wear indicators 336.

Figure 11:
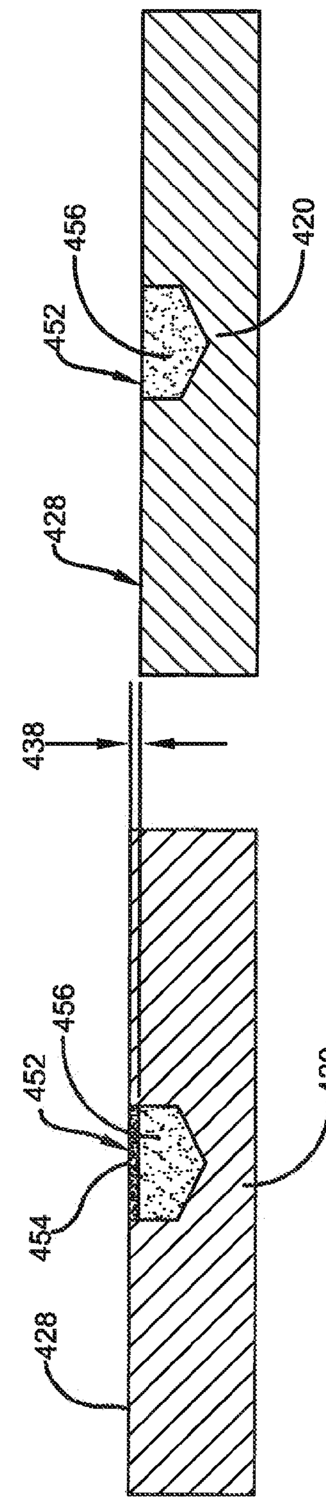
FIG. 11 is a sectional side view of exemplary guidance members according to the principles of the present disclosure.

FIG. 11 is analogous to FIG. 3. FIG. 11 is a comparative illustration of another exemplary guidance member 420. The guidance member 420 is shown generally in an initial condition on the left side of FIG. 11 and in a worn condition on the right side of FIG. 11. A visually-detectable wear indicator 452 is disposed in the guidance member 420. It will be appreciated that while one visually-detectable wear indicator 452 is shown associated with guidance member 420, guidance member 420 may include a plurality of wear indicators 452. The visually-detectable wear indicator 452 is formed from a plurality of differently colored layers 454 and 456. A junction of two layers 454, 456 is defined at the depth 438. The layer 456 is a portion of the wear indicator 452 that is recessed from a guiding surface 428 in a wear indicator cavity. The depth 438 corresponds to an extent of acceptable wear of the guiding surface 428. In operation, the layer 454 can be worn away, exposing the differently-colored layer 456. When the layer 456 is exposed and visually-detectable by the human operator, the human operator can determine that the guidance member 420 should be replaced or refurbished. It will be appreciated that the differently color layers 454 and 456 can be provided or included in the various wear indicator cavities discussed herein.

It should be understood that the mixing and matching of features, elements, methodologies and/or functions between various examples may be expressly contemplated herein so that one skilled in the art would appreciate from the present teachings that features, elements and/or functions of one example may be incorporated into another example as appropriate, unless described otherwise above.

What is claimed is:

1. A stamping die, comprising:

an upper die member;

a lower die member, the upper and lower die members movable relative to one another in reciprocating motion along an axis to generate work-pieces; and at least one guidance member removably positioned on at least one of the upper and lower die members and having a guiding surface operably disposed to guide relative movement between the upper and lower die members, the at least one guidance member having at least one wear indicator cavity recessed from the guiding surface, wherein a depth of the at least one wear indicator cavity from the guiding surface corresponds to an extent of acceptable wear of the guiding surface such that the at least one wear indicator cavity allows for visual inspection of the extent of wear of the at least one guidance member while the at least one guidance member is positioned on at least one of the upper and lower die members.

2. The stamping die of claim 1, wherein the at least one guidance member further comprises:

a first guidance member affixed to the upper die member;

a second guidance member affixed to the lower die member, wherein the guiding surface of the first guidance member slides along the guiding surface of the second guidance member;

a third guidance member affixed to the upper die member; and a fourth guidance member affixed to the lower die member, wherein the guiding surface of the third guidance member slides along the guiding surface of the fourth guidance member, wherein the first and third guidance members are separate from each other and the second and fourth guidance members are separate from each other.

3. The stamping die of claim 2, wherein the first and second guidance members are formed from different materials.

4. The stamping die of claim 3, wherein the at least one wear indicator cavity of the first guidance member and the at least one wear indicator cavity of the second guidance member are similarly shaped.

5. The stamping die of claim 1, wherein the at least one wear indicator cavity is shaped as at least one rectangular channel.

6. The stamping die of claim 5, wherein the at least one wear indicator cavity extends along the axis of reciprocating motion.

7. The stamping die of claim 1, wherein the at least one wear indicator cavity is shaped as at least one circle.

8. The stamping die of claim 1, wherein the at least one wear indicator cavity is shaped as at least one channel, the depth of the channel being constant along a width of the channel.

9. The stamping die of claim 8, wherein the at least one wear indicator cavity further comprises first and second wear indicator cavities, each being shaped as a channel.

10. The stamping die of claim 9, wherein the first and second wear indicator cavities are spaced from one another and extend parallel to the axis of reciprocating motion.

11. The stamping die of claim 8, wherein the at least one wear indicator cavity further comprises first and second wear indicator cavities, each extending in a different plane.

12. The stamping die of claim 1, wherein the at least one guidance member is further defined as a bushing and the guiding surface is an aperture.

13. The stamping die of claim 12, wherein the at least one wear indicator cavity further comprises first, second and third wear indicator cavities evenly spaced about the aperture and each being shaped as a channel.

14. A method of operating a stamping die comprising the steps of:

moving an upper die member and a lower die member relative to one another in reciprocating motion along an axis to generate work-pieces;

guiding relative movement of the upper and lower die members with at least one guidance member having a guiding surface, the at least one guidance member being removably positioned on at least one of the upper and lower die members;

providing at least one visually-detectable wear indicator cavity in the at least one guidance member recessed from the guiding surface, the wear indicator cavity having a substantially constant depth corresponding to an extent of acceptable wear of the guiding surface; and determining whether the guiding surface is within the extent of acceptable wear by detecting whether the wear indicator cavity remains recessed below the guiding surface while the at least one guidance member is positioned on at least one of the upper and lower die members.

15. The method of claim 14, wherein determining whether the guiding surface is within the extent of acceptable wear includes visually inspecting the guidance member and wear indicator cavity while the guidance member is positioned on at least one of the upper and lower die members to determine whether the wear indicator cavity remains recessed below the guiding surface.

16. The method of claim 14, further comprising the step of:

providing the at least one visually-detectable wear indicator cavity open to the guiding surface.

17. The method of claim 14, wherein providing at least one visually-detectable wear indicator cavity in the guidance member includes providing two visually-detectable wear indicator cavities in the guidance member; and wherein determining whether the guiding surface is within the extent of acceptable wear includes determining whether the two wear indicator cavities remain recessed below the guiding surface and whether one of the two wear indicator cavities exhibits a different depth than the other of the two wear indicator cavities.

18. The stamping die of claim 1, wherein the at least one wear indicator cavity comprises:

a first colored layer; and a second colored layer having a different color than the first colored layer, the second colored layer disposed adjacent the first colored layer such that a junction is formed between the first and second colored layers, wherein the junction corresponds to the depth of the at least one wear indicator cavity corresponding to the extent of acceptable wear.

* * * * *